US00PP15007P2

(12) United States Plant Patent
Bergman

(10) Patent No.: US PP15,007 P2
(45) Date of Patent: Jul. 13, 2004

(54) CHRYSANTHEMUM PLANT NAMED 'RED YOAUBURN'

(50) Latin Name: *Chrysanthemum×morifolium*
Varietal Denomination: Red Yoauburn

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/676,783

(22) Filed: Oct. 1, 2003

(51) Int. Cl.[7] ..... A01H 5/00

(52) U.S. Cl. ..... Plt./298

(58) Field of Search ..... Plt./298, 286

*Primary Examiner*—Bruce R. Campell
*Assistant Examiner*—June Hwu
(74) *Attorney, Agent, or Firm*—C. A. Whealy

(57) ABSTRACT

A distinct cultivar of Chrysanthemum plant named 'Red Yoauburn', characterized by its uniform and outwardly spreading plant habit; strong and freely branching growth habit; dark green-colored foliage; uniform flowering response and habit; early flowering habit; numerous daisy-type inflorescences; red-colored ray florets that resist fading; and good postproduction longevity with plants maintaining good substance and color for about three weeks in an interior environment

2 Drawing Sheets

Botanical classification/cultivar designation: *Chrysanthemum×morifolium* cultivar Red Yoauburn.

BACKGROUND OF THE INVENTION

The present Invention relates to a new and distinct cultivar of Chrysanthemum plant, botanically known as *Chrysanthemum×morifolium* and hereinafter referred to by the name 'Red Yoauburn'.

The new Chrysanthemum is a product of a planned breeding program conducted by the Inventor in Fort Myers, Fla. The objective of the program is to create or discover new potted Chrysanthemum cultivars that are suitable for year-round production with uniform plant growth habit, good vigor and strong branching habit, numerous inflorescences, desirable inflorescence form and floret colors, fast and uniform flowering response, and good postproduction longevity.

The new Chrysanthemum is a naturally-occurring whole plant mutation of the Chrysanthemum cultivar Yoauburn, disclosed in U.S. Plant Pat. No. 12,526. The new Chrysanthemum was discovered and selected by the Inventor as a single flowering plant from within a population of flowering plants of Yoauburn in February, 2000, in a controlled environment in Fort Myers, Fla. The selection of this plant was based on its uniform plant growth habit, good vigor and strong branching habit, numerous inflorescences, desirable inflorescence form and floret colors, fast and uniform flowering response, and good postproduction longevity.

Asexual reproduction of the new Chrysanthemum by vegetative tip cuttings was first conducted in Fort Myers, Fla. in May, 2000. Asexual reproduction by cuttings has shown that the unique features of this new Chrysanthemum are stable and reproduced true to type in successive generations.

SUMMARY OF THE INVENTION

The cultivar Red Yoauburn has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Red Yoauburn'. These characteristics in combination distinguish 'Red Yoauburn' as a new and distinct Chrysanthemum:

1. Uniform and outwardly spreading plant habit.
2. Strong and freely branching growth habit.
3. Dark green-colored foliage.
4. Uniform flowering response and habit.
5. Early flowering, 8-week response time.
6. Numerous daisy-type inflorescences.
7. Red-colored ray florets that resist fading.
8. Good postproduction longevity with plants maintaining good substance and color for about three weeks in an interior environment.

Plants of the new Chrysanthemum differ primarily from plants of the cultivar Yoauburn primarily in ray floret coloration as plants of the cultivar Yoauburn have orange bronze-colored ray florets. In addition, plants of the new Chrysanthemum are more vigorous than plants of the cultivar Yoauburn.

Plants of the new Chrysanthemum can be compared to plants of the cultivar Rage, disclosed in U.S. Plant Pat. No. 8,770. In side-by-side comparisons conducted in Fort Myers, Fla., plants of the new Chrysanthemum differed from plants of the cultivar Rage in the following characteristics:

1. Plants of the new Chrysanthemum were more outwardly spreading than plants of the cultivar Rage.
2. Ray florets of plants of the new Chrysanthemum were deeper red in color than ray florets of plants of the cultivar Rage.
3. Plants of the new Chrysanthemum did not produce pollen whereas plants of the cultivar Rage produced moderate to abundant pollen.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of typical flowering plants of 'Red Yoauburn'.

The photograph on the second sheet comprises a close-up view of typical inflorescences of 'Red Yoauburn'.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the spring in Salinas, Calif. in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At the time of the pinch, the photoinductive short day/long night treatments were initiated. Plants used for the photographs and description were grown as spray-types. Measurements and numerical values represent averages of typical flowering plants.

Botanical classification: *Chrysanthemum×morifolium* cultivar Red Yoauburn.

Commercial classification: Daisy-type potted Chrysanthemum.

Parentage: Naturally-occurring whole plant mutation of Yoauburn, disclosed in U.S. Plant Pat. No. 12,526.

Propagation:

*Type*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous daisy-type potted Chrysanthemum that is typically grown as a spray-type. Uniform with lateral branches outwardly spreading; uniformly mounded crown. Strong and freely branching growth habit; about four lateral branches develop after removal of terminal apex (pinching); dense and full plants.

*Plant height.*—About 25 cm.

*Plant width.*—About 31 cm.

*Lateral branches.*—Length: About 19 cm. Diameter: About 4.5 mm. Internode length: About 1 cm. Strength: Strong. Texture: Pubescent. Color: 146A.

*Foliage description.*—Arrangement: Alternate; simple. Length: About 6.5 cm. Width: About 5.1 cm. Apex: Mucronate. Base: Truncate. Margin: Palmately lobed, sinuses between lateral lobes parallel to divergent. Texture, upper and lower surfaces: Pubescent. Color: Developing foliage, upper and lower surfaces: Closest to 147A. Fully expanded foliage, upper surface: Closest to 147B. Fully expanded foliage, lower surface: Lighter than 147B. Venation, upper surface: 147A. Venation, lower surface: 147B. Petiole length: About 2.2 cm. Petiole diameter: About 3 mm. Petiole color, upper and lower surfaces: 147B.

Inflorescence description:

*Appearance.*—Daisy-type inflorescence form with elongated oblong-shaped ray florets. Inflorescences borne on terminals above foliage. Disk and ray florets develop acropetally on a capitulum. Inflorescences not fragrant. Plants are typically grown as spray-types.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity.*—Inflorescences maintain good color and substance for about three weeks in an interior environment.

*Quantity of inflorescences.*—About seven inflorescences per lateral branch.

*Inflorescence bud.*—Height: About 6 mm. Diameter: About 8 mm. Shape: Oblate. Color: Close to 146A.

*Inflorescence diameter.*—About 6.5 cm.

*Inflorescence depth (height).*—About 2.2 cm.

*Diameter of disc.*—About 1.4 cm.

*Receptacle diameter.*—About 5 mm.

*Ray florets.*—Shape: Elongated oblong. Orientation: Initially upright, then perpendicular to the peduncle. Aspect: Mostly flat. Length: About 3.2 cm. Corolla tube length: About 6 mm. Width: About 1.1 cm. Apex: Acute to emarginate. Base: Fused into a corolla tube. Margin: Entire. Texture: Smooth, glabrous, satiny. Number of ray florets per inflorescence: About 34 arranged in three or four whorls. Color: When opening and fully opened, upper surface: 9A overlain with 53A. When opening, lower surface: 5A underlain with close to 53A. Fully opened, lower surface: Close to 6C faintly underlain with close to 53A.

*Disc florets.*—Arrangement: Massed at center of receptacle. Shape: Tubular, elongated. Apex: Five-pointed. Length: About 6 mm. Diameter, apex: About 2 mm. Diameter, base: About 1 mm. Number of disc florets per inflorescence: About 72. Color: Immature: Close to 6A. Mature: Apex: Close to 9A. Mid-section and base: Close to 155D.

*Phyllaries.*—Quantity per inflorescence: About 23. Length: About 6 mm. Width: About 2 mm. Shape: Deltoid. Apex: Acute. Base: Truncate. Margin: Entire. Texture, upper surface: Waxy, smooth. Texture, lower surface: Pubescent. Color, upper surface: Close to 146A. Color, lower surface: Close to 146A to 146B.

*Peduncles.*—Length: First peduncle: About 2.5 cm. Fourth peduncle: About 5 cm. Seventh peduncle: About 6.1 cm, Diameter: About 2 mm. Angle to vertical: About 50° from vertical. Strength: Strong, flexible. Texture: Pubescent. Color: Closest to 146A.

*Reproductive organs.*—Androecium: Present on disc florets only. Anther color: Close to 9A. Pollen amount: None observed. Gynoecium: Present on both ray and disc florets. Style color: Close to 144B to 144C. Stigma color: Close to 9A.

*Seed/fruit.*—Seed and fruit production has not been observed.

Disease/pest resistance: Resistance to pathogens and pests common to Chrysanthemums has not been observed on plants grown under commercial greenhouse conditions.

It is claimed:

1. A new and distinct cultivar of Chrysanthemum plant named 'Red Yoauburn', as illustrated and described.

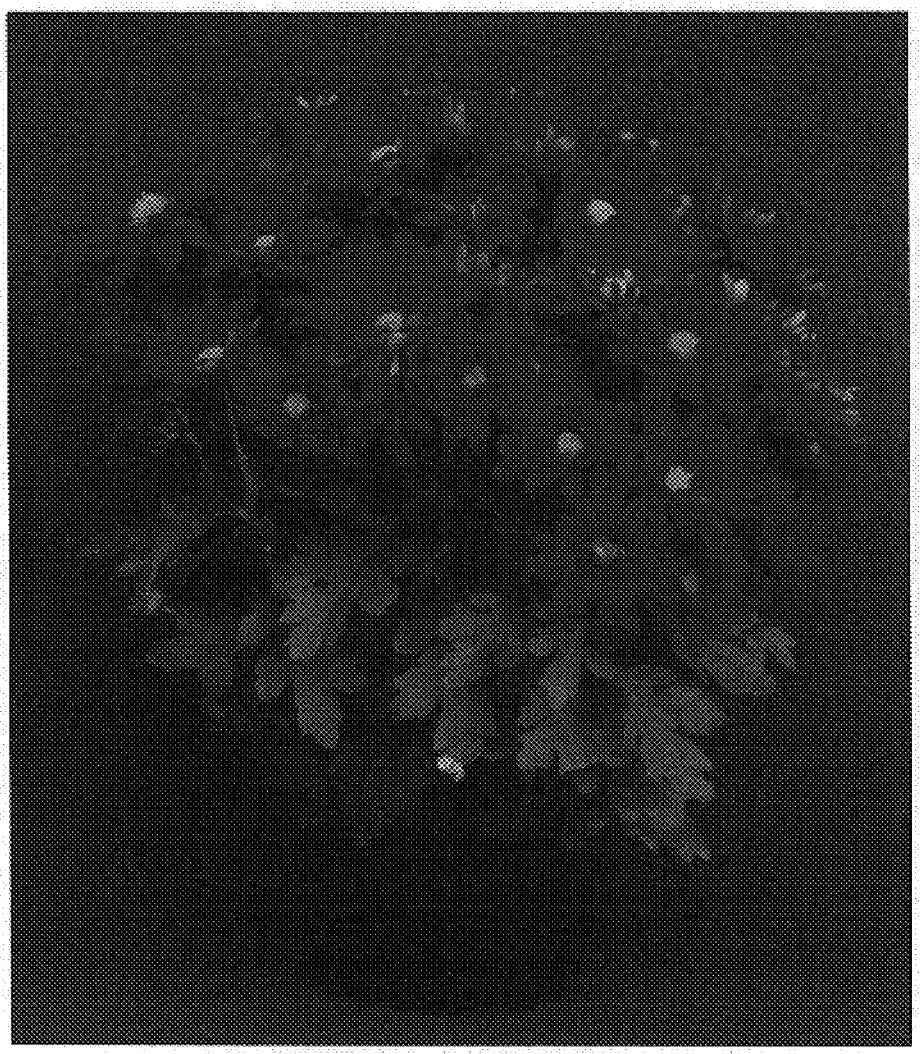

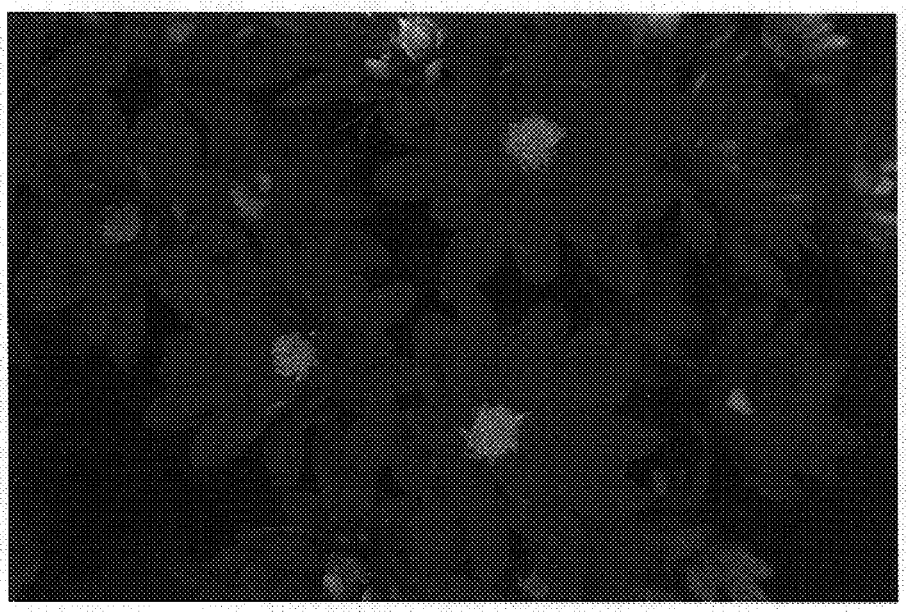

* * * * *